US009096547B2

(12) United States Patent
Takakura et al.

(10) Patent No.: US 9,096,547 B2
(45) Date of Patent: Aug. 4, 2015

(54) SODIUM SALT OF 6-FLUORO-3-HYDROXY-2-PYRAZINE CARBOXAMIDE

(71) Applicant: Toyama Chemical Co., Ltd., Tokyo (JP)

(72) Inventors: Keiko Takakura, Toyama (JP); Namika Nakamatsu, Toyama (JP); Sakiko Takeshima, Toyama (JP); Sayuri Uehara, Toyama (JP)

(73) Assignee: TOYAMA CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/515,673

(22) Filed: Oct. 16, 2014

(65) Prior Publication Data

US 2015/0038713 A1 Feb. 5, 2015

Related U.S. Application Data (62) Division of application No. 13/876,998, filed as application No. PCT/JP2011/072333 on Sep. 29, 2011.

(30) Foreign Application Priority Data

Sep. 30, 2010 (JP) ................. 2010-221682

(51) Int. Cl.
*C07D 241/24* (2006.01)
*A61K 9/19* (2006.01)

(52) U.S. Cl.
CPC ............... *C07D 241/24* (2013.01); *A61K 9/19* (2013.01)

(58) Field of Classification Search
CPC .................................................. C07D 241/24
See application file for complete search history.

(56) References Cited

U.S. PATENT DOCUMENTS

| 6,787,544 | B2 | 9/2004 | Furuta et al. |
| 6,800,629 | B2 | 10/2004 | Egawa et al. |
| 8,168,789 | B2 | 5/2012 | Takamatsu et al. |
| RE43,748 | E | 10/2012 | Furuta et al. |
| 2002/0013316 | A1 | 1/2002 | Furuta et al. |
| 2010/0087447 | A1 | 4/2010 | Maekawa |
| 2012/0010221 | A1 | 1/2012 | Kakuda et al. |
| 2013/0217708 | A1 | 8/2013 | Takakura et al. |

FOREIGN PATENT DOCUMENTS

| CN | 101610772 | 12/2009 |
| EP | 1 051 978 | 11/2000 |
| EP | 1 112 743 A1 | 7/2001 |
| JP | 3413406 | 6/2003 |
| JP | 2008-231064 | 10/2008 |
| JP | 2008 231067 | 10/2008 |
| WO | 00 10569 | 3/2000 |
| WO | WO 2009/041473 | 4/2009 |

OTHER PUBLICATIONS

Searles et al. Annealing to optimize the primary drying rate, reduce freezing-induced drying rate heterogeneity, and determine T(g)' in pharmaceutical lyophilization. Journal of Pharmaceutical Sciences, 2001, 90, 872.*
Keiko Toyo Seizai no Sekkei to Hyoka, Kabushiki Kaisha Yakugyo Jihosha, pp. 69-85, (Feb. 10, 1995).
Chushazai-sono Kiso to Chozai to Tekiyo—, 1$^{st}$ edition, Nanzando Co., Ltd., pp. 19-25, (Mar. 22, 1995).
International Search Report Issued Nov. 15, 2011 in PCT/JP11/72333 Filed Sep. 29, 2011.
Swarbrick, et al. (eds. Encyclopedia of Pharmaceutical Technology 13 (Marcel Dekker, NY 1996) pp. 453-499.
Extended European Search Report issued Feb. 24, 2014 in Patent Application No. 11829253.1.
Gennaro, A. R. et al., p. 704, paragraph "Salt Expansion"—p. 706, p. 802, paragraph "Freeze Drying"—p. 803, Remington: The Science and Practice of Pharmacy 20$^{th}$ Edition, XP-002719882, 2000, 5 pages.
Furniss, B. S. et al., "Sublimation Techniques—Freeze Drying", Vogel's Textbook of Practical Organic Chemistry 5$^{th}$ Edition, XP-002719883, 1996, 4 pages.
Lian Yu et al., "Amorphous Pharmaceutical Solids: Preparation, Characterization and Stabilization", Advanced Drug Delivery Reviews, vol. 48, No. 1, XP-009065056, May 16, 2001, pp. 27-42.
Office Action in Chinese application No. 201180055060.8, dated Apr. 23, 2014. (w/English Translation).
Keiko Toyo Seizai no Sekkei to Hyoka, Kabushiki Kaisha Yakugyo Jihosha, Feb. 10, 1995, pp. 69-85.
U.S. Appl. No. 14/508,185, filed Oct. 7, 2014, Takakura, et al.

\* cited by examiner

*Primary Examiner* — Brian McDowell
(74) *Attorney, Agent, or Firm* — Oblon, McClelland, Maier & Neustadt, L.L.P.

(57) ABSTRACT

A preparation replete with crystals of a sodium salt of 6-fluoro-3-hydroxy-2-pyrazine carboxamide has superior solubility, and is useful as a preparation for injection.

1 Claim, 6 Drawing Sheets

SODIUM SALT OF 6-FLUORO-3-HYDROXY-2-PYRAZINE CARBOXAMIDE

This application is a divisional of U.S. patent application Ser. No. 13/876,998 filed Jun. 26, 2013, pending, which is a National Stage of PCT/JP11/072333 filed Sep. 29, 2011 and claims the benefit of JP 2010-221682 filed Sep. 30, 2010.

TECHNICAL FIELD

The present invention relates to a crystal of sodium salt of 6-fluoro-3-hydroxy-2-pyrazinecarboxamide (hereinafter referred to as "Compound A"), an injectable preparation containing the same, and a process thereof.

BACKGROUND ART

These days, worldwide pandemic has been caused by H1N1 influenza virus, and occurrence of pandemic by a further virulent virus in the future is a concern.

At present, as therapeutic agents for influenza, e.g., Oseltamivir, Zanamivir, Peramivir, Laninamivir, and Amantadine are used. However, these therapeutic agents have, for example, the following drawbacks. Oseltamivir cannot be administered to patients having difficulty in oral administration. It is difficult to administer Zanamivir to children and aged persons. It takes a long time to administer Peramivir. Amantadine is ineffective against Type B influenza virus and resistant viruses have emerged. Laninamivir is an inhalation drug, which is not suitable to patients with dementia and a severe disease, and it is difficult to administer it to children.

A further superior therapeutic agent for influenza has been desired. Particularly, an injection that can be administered to patients having difficulty in oral administration, children, and aged persons has been desired.

Meanwhile, many reports have been published on methods for improving solubility of medicinal compounds in water. For example, a method for improving the solubility in water by changing the state of a water-insoluble medicinal compound into an amorphous state is known. In general, an amorphous state of a compound exhibits more superior solubility in water than a crystalline state thereof (PATENT DOCUMENT 1).

Compound A or a salt thereof has a superior antiviral activity and is useful as a therapeutic agent for viral infection (PATENT DOCUMENT 2). However, Compound A has low solubility in water, and thus an injection of Compound A or a salt thereof has not been known yet.

The present inventors prepared an aqueous solution of a sodium salt of Compound A by using sodium hydroxide generally used as a base, and then produced a lyophilized preparation in accordance with a common method, for improving the water solubility of Compound A. The sodium salt of Compound A obtained by this process was an amorphous dry powder, thus quick dissolution thereof in water was expected. However, contrary to the expectation, the obtained lyophilized preparation was a lyophilized cake having poor solubility, and required a long time to dissolve. To describe more specifically, when a solvent was added to the lyophilized preparation, the lyophilized cake changed into a poorly soluble mass substance that took a long time to dissolve. The amorphous lyophilized preparation of a sodium salt of Compound A was a preparation needing a long time to dissolve, and was difficult to handle with significant loss of convenience in use.

Meanwhile, as a method for preparing a lyophilized preparation, a process having an annealing step provided therein is known. However, the effect of the annealing step on the solubility of a lyophilized preparation differs depending on substances. Therefore, studies have been made in a trial-and-error manner (NON-PATENT DOCUMENT 1).

PRIOR ARTS REFERENCES

Patent Documents

PATENT DOCUMENT 1: JP 3413406
PATENT DOCUMENT 2: International Publication No. WO 00/10569 pamphlet
NON-PATENT DOCUMENT 1: Development of medicinal drug, Vol. 11, page 393, 2000

DISCLOSURE OF THE INVENTION

Problem to be Solved by the Invention

There is a need for the development of an injectable preparation of Compound A or a salt thereof with superior solubility.

Means for Solving the Problems

The present inventors have intensively conducted studies with the view to attaining the above desire. As a result, they have found that
(1) the solubility of a sodium salt of Compound A (hereinafter referred to as "Salt A") in water is high,
(2) the dissolution rate of a crystal of Salt A, and the dissolution rate of a milled crystal of Salt A are significantly high, and
(3) a preparation containing a crystal of Salt A and/or a milled crystal of Salt A is superior in solubility.

More specifically, a crystal of Salt A can be produced by precipitating a crystal from a solution of Salt A. The crystal has high solubility and significantly high dissolution rate in water. Thus, a preparation containing a crystal of Salt A is superior in solubility and useful as an injectable preparation.

Furthermore, a milled crystal of Salt A has high solubility and significantly high dissolution rate in water. Thus, a preparation containing a milled crystal of Salt A is superior in solubility and useful as an injectable preparation.

A powder filling method is known as a technique for filling a vial, etc. with a powder. However, in a powder filling method, it is difficult to accurately control the filler content, and contamination with minute foreign bodies occurs easily, when compared to a method that divides a solution into small portions. For these reasons, as a process for producing a solid injection, a process by lyophilization is the most reliable process.

As a result of intensive studies, the present inventors have found that a lyophilized preparation of a crystal of Salt A having significantly high dissolution rate can be produced in a short crystallization time by controlling the concentration range, the pH range, and the temperature (crystallization temperature) range in a temperature-increasing step after primary freezing in lyophilization of an aqueous solution of Salt A to be subjected to lyophilization. More specifically, a crystal of Salt A can be produced by providing a step of increasing temperature after the primary freezing of lyophilization. The resultant crystal has high solubility in water and significantly high dissolution rate, even though it is not milled. Therefore, the preparation containing the crystal is superior in solubility and useful as an injectable preparation.

As a result of intensive studies conducted repeatedly, the present inventors have found that a further superior lyophilized preparation can be produced by adding additives to an aqueous solution of Salt A to be subjected to lyophilization. In such a manner, the present invention has been accomplished.

Meanwhile, it is known that a crystalline state changes to an amorphous state when water is removed from the crystal of a hydrate (Yu L., Advanced Drug Delivery Reviews, Vol. 48, page 29, 2001).

However, the crystal of Salt A of the present invention does not change to an amorphous state even if a dehydration operation is applied during lyophilization. In addition, a lyophilized preparation of Salt A of the present invention has significantly higher dissolution rate and much higher stability, compared to the amorphous lyophilized preparation.

A superior lyophilized preparation of a crystal of Salt A can be produced according to the process of the present invention. The lyophilized preparation can be easily maintained in aseptic conditions and from which insoluble foreign bodies can be easily removed. Therefore, the lyophilized preparation is an injection superior in usability.

More specifically, the present invention is as follows:
1. A crystal of Salt A or a hydrate thereof. This crystal thereof has high solubility in water and significantly high dissolution rate.
2. An injectable preparation containing a crystal of Salt A or a hydrate thereof. The injectable preparation is superior in solubility.
3. A lyophilized preparation containing a crystal of Salt A. The lyophilized preparation is superior in solubility.
4. A process for producing a lyophilized preparation containing a crystal of Salt A, including the following steps: (1) cooling an aqueous solution containing Salt A to produce a frozen product, (2) increasing the temperature of the frozen product, (3) further cooling the frozen product, and (4) carrying out lyophilization. The process can produce a lyophilized preparation of a crystal of Salt A which has significantly high dissolution rate in a short crystallization time.
5. The process according to 4 above, wherein the achieving temperature of the frozen product falls within the range of −15 to −5° C. in the step of increasing the temperature of the frozen product. By setting the temperature of the frozen product so as to fall within the range of −15 to −5° C., a further superior lyophilized preparation of a crystal of Salt A can be produced.

Advantages of the Invention

A crystal of Salt A of the present invention is superior in solubility in water and useful as a drug substance of an injectable preparation.

Furthermore, a preparation containing a crystal of Salt A of the present invention is useful as an injectable preparation that is superior in solubility and stability.

Moreover, the process for producing a crystal of Salt A of the present invention is useful as a process for producing a lyophilized preparation of a crystal of Salt A that is superior in solubility and stability.

MODE FOR CARRYING OUT THE INVENTION

Hereinafter, the present invention will be described in detail.

Compound A can be produced by a method described, for example, in PATENT DOCUMENT 2. Compound A has a tautomer: 6-fluoro-3-oxo-3,4-dihydro-2-pyrazinecarboxamide. This tautomer is included in the present invention.

A crystal of Salt A of the present invention and an injectable preparation containing a crystal of Salt A can be produced, for example, according to the following processes.

Process 1: Crystal of Salt A Hydrate 1

A crystal of Salt A Hydrate 1 can be produced by adding Compound A and base to water, heating the mixture to dissolve, adding 2-propanol, and collecting a precipitated crystal by filtration.

The amount of water is satisfactorily 1 to 50 times (v/w), and preferably 5 to 10 times (v/w) as large as that of Compound A.

Examples of base include sodium hydroxide, sodium carbonate, and sodium hydrogen carbonate.

The amount of base is satisfactorily 1.0 equivalent or more, and preferably 1.0 to 1.5 equivalent of Compound A.

The temperature of the reaction with base is satisfactorily 30 to 100° C., and preferably 40 to 80° C.

The amount of 2-propanol is satisfactorily 5 to 100 times (v/w), and preferably 10 to 30 times (v/w) as large as that of Compound A.

An injectable preparation can be produced by filling a vial, etc. with the crystal of Salt A Hydrate 1 and/or the milled crystal of Salt A Hydrate 1 thus obtained.

Process 2: Crystal of Salt A Hydrate 2

A crystal of Salt A Hydrate 2 can be produced by adding Compound A and base to water, dissolving the mixture, cooling the aqueous solution, and collecting a precipitated crystal by filtration.

The amount of water is satisfactorily 1 to 50 times (v/w), and preferably 5 to 20 times (v/w) as large as that of Compound A.

Examples of base include sodium hydroxide, sodium carbonate, and sodium hydrogen carbonate.

The amount of base is satisfactorily 0.8 to 2 equivalent, and preferably 0.9 to 1.1 equivalent of Compound A.

The temperature of the reaction with base is satisfactorily 0 to 100° C., and preferably 5 to 40° C.

The cooling temperature of crystallization operation is satisfactorily 0 to 20° C., and preferably 0 to 5° C.

An injectable preparation can be produced by filling a vial, etc. with the crystal of Salt A Hydrate 2 and/or the milled crystal of Salt A Hydrate 2 thus obtained.

Process 3: Crystal of Salt A anhydrate

A crystal of Salt A anhydrate can be produced by allowing a crystal of Salt A Hydrate 2 to stand still at −20 to 60° C. under reduced pressure.

The standstill time is satisfactorily 0.5 to 120 hours, and preferably 1 to 72 hours.

The degree of pressure reduction is not particularly limited however, it is satisfactorily 100 Pa or below, and preferably 50 Pa or below.

Alternatively, a crystal of Salt A anhydrate can be produced by allowing a crystal of Salt A Hydrate 2 to stand still under heating.

The heating temperature is satisfactorily 30° C. or above, preferably 50° C. to 300° C., and more preferably 50° C. to 150° C.

An injectable preparation can be produced by filling a vial, etc. with the crystal of Salt A anhydrate and/or the milled crystal of Salt A anhydrate thus obtained.

Alternatively, an injectable preparation of a Salt A anhydrate can be produced by grinding the crystal of Salt A Hydrate 2 and then drying it in the same manner as mentioned above.

Process 4: Crystal of Salt A (Lyophilization)

(1) First Step (Primary Freezing Step)

A frozen product can be obtained by freezing an aqueous solution of Compound A and base.

The amount of water is satisfactorily 10 to 100 times (v/w), and preferably 10 to 50 times (v/w) as large as that of Compound A.

Examples of base include sodium hydroxide, sodium carbonate, and sodium hydrogen carbonate. These may be used alone or as a mixture of two or more types.

The pH of the aqueous solution is satisfactorily 4.0 to 10, and preferably 6.5 to 8.5.

The temperature of the primary freezing step is satisfactorily a collapse temperature or below, and preferably −60 to −30° C.

The period of time for the primary freezing step is satisfactorily 1 to 10 hours, and preferably 2 to 5 hours.

(2) Second Step (Annealing Step)

The temperature of the frozen product is increased and the frozen product is maintained for a preset time (annealing) to allow crystallization to proceed to obtain a crystalline frozen product.

The temperature, at which thawing of the frozen product dose not occur and crystallization proceeds to the extent that the frozen product maintains a frozen state, may be satisfactory in the annealing step; preferably −20 to −2° C., and more preferably −15 to −5° C.

The period of time for maintaining the annealing step is satisfactorily 0.5 to 48 hours, and preferably 1 to 24 hours.

(3) Third Step (Secondary Freezing Step)

Subsequently, the crystalline frozen product is cooled again.

The temperature of the secondary freezing step is preferably −60 to −30° C.

The period of time for the secondary freezing step is satisfactorily 1 to 10 hours, and preferably 1 to 5 hours.

(4) Fourth Step (Lyophilization Step)

Subsequently, pressure reduction treatment can be performed to produce a lyophilized preparation.

This step can be performed in accordance with a lyophilization method usually used, for example, in two steps, i.e., a primary drying step and a secondary drying step.

The primary drying step is carried out under reduced pressure while product temperature is maintained at the eutectic point or below; however, since the temperature drops as the moisture sublimates from the frozen product, the preset temperature of apparatus may be the eutectic point or above.

The temperature of the frozen product is satisfactorily −40 to −3° C., and preferably −30 to −5° C.

The preset temperature of apparatus is satisfactorily −20 to 60° C., and preferably −10 to 50° C.

The degree of pressure reduction in the primary drying step is not particularly limited; however, it is satisfactorily 100 Pa or below, and preferably 50 Pa or below.

As the amount of sublimating moisture decreases, the rate of temperature decrease becomes slower. As a result, the product temperature increases and becomes almost equal to the preset temperature. Usually, at this time point, the primary drying step is determined to have completed.

Subsequently, the secondary drying step is carried out.

The secondary drying step is carried out at room temperature or more, and preferably 30 to 60° C.

In the secondary drying step, the degree of pressure reduction is preferably enhanced in order to accelerate removal of water. The degree of pressure reduction is satisfactorily 0.5 to 50 Pa, and preferably 1 to 5 Pa.

The secondary drying step may be satisfactorily carried out up until the point where the product temperature becomes almost equal to the preset temperature and a product temperature virtually does not change.

The powder X-ray diffraction pattern of a crystal of Salt A produced by the process was the same as the powder X-ray diffraction pattern of a crystal of Salt A anhydrate produced in process 3. That is, a lyophilized preparation of a crystal of Salt A anhydrate can be produced by the use of the process.

In the process for producing the lyophilized preparation of the present invention, a sterilization treatment or the like may be carried out in accordance with the procedure usually employed.

In the process of the present invention, since no organic solvents are used, the lyophilized preparation has no residual solvent.

The lyophilized preparation of the present invention is not harmful to a human body.

Unless otherwise, powder X-ray diffraction measurement conditions are as follows.

Powder X-ray diffraction measurement conditions:
X-rays to be used: CuKα
Applied voltage: 40 kV
Supplied current: 40 mA
Scanning axis: 2θ
Scanning range: 2θ=2 to 40°

The characteristic peaks of powder X-ray diffraction sometimes varies depending on measurement conditions. Generally, 2θ has a margin of error of ±0.2°. Accordingly, "the diffraction angle of X° represented by 2θ" refers to "a diffraction angle of ((X−0.2) to (X+0.2))° represented by 2θ".

The crystal of Salt A of the present invention includes a crystal of Hydrate 1, a crystal of Hydrate 2, and a crystal of an anhydrate. Furthermore, various shapes of crystals are included in the crystal.

Additives can be added to the lyophilized preparation containing Salt A of the present invention for improving solubility.

The temperature range of the annealing step can be extended by adding additives.

Examples of the additives include amino acids, polyethers, saccharides, sugar alcohols, salts, urea, ethyl urea, creatinine, nicotinic acid amide, trometamol, purified soybean lecithin, egg albumin, bovine serum albumin, and polysorbates. These may be used alone or as a mixture of two or more types.

Examples of the amino acids include glycine, L-alanine, L-phenylalanine, L-valine, L-leucine, L-isoleucine, taurine, DL-methionine, L-threonine, L-glutamine, sodium L-glutamate, acetyltryptophan, and L-histidine. L-alanine, L-phenylalanine, L-valine, L-leucine, L-isoleucine, taurine, DL-methionine, L-glutamine, and L-histidine are more preferable, and L-leucine, L-isoleucine, and L-valine are further preferable.

Examples of the polyethers include polyethylene glycol 300, polyethylene glycol 400, polyethylene glycol 600, and polyethylene glycol 4000. Polyethylene glycol 400 is more preferable.

Examples of the saccharides include trehalose, maltose, glucose, lactose, purified white sugar, fructose, dextran 40, and cyclodextrin. Dextran 40 is more preferable.

Examples of the sugar alcohols include D-sorbitol, xylitol, inositol, and D-mannitol.

Examples of the salts include sodium acetate, sodium lactate, sodium L-tartrate, sodium citrate, sodium salicylate, sodium benzoate, and sodium caprylate.

Examples of the polysorbates include polysorbate 20 and polysorbate 80. Polysorbate 80 is more preferable.

Examples of preferable additives include amino acids, polyethers, saccharides, urea, and polysorbates.

Furthermore, at the First step of process 4, solubility of a lyophilized preparation can be improved by controlling the pH of an aqueous solution of Compound A and base.

The pH of the aqueous solution of Compound A and base is satisfactorily 4.0 to 10, preferably 6.5 to 8.5, and more preferably 6.5 to 7.5.

Furthermore, if necessary, conventional additives, such as an osmo-regulator, a pH regulator, a buffer, a solubilizer, a stabilizer, a surfactant, a soothing agent, and/or a preservative, may be added to the preparation of the present invention.

Examples of the osmo-regulator include sodium chloride, glycerin, and propylene glycol.

Examples of the pH regulator and/or the buffer include acids such as hydrochloric acid, phosphoric acid, sulfuric acid, methanesulfonic acid, acetic acid, lactic acid, maleic acid, citric acid, tartaric acid, ascorbic acid, and benzoic acid; salts such as sodium bicarbonate, sodium carbonate, sodium dihydrogenphosphate, potassium dihydrogenphosphate, disodium hydrogenphosphate, dipotassium hydrogenphosphate, trisodium phosphate, disodium citrate, sodium deoxycholate, and sodium sulfite; and bases such as sodium hydroxide, trometamol, monoethanolamine, diethanolamine, triethanolamine, L-arginine, and L-lysine.

Examples of the solubilizer include Macrogol and purified soybean lecithin.

Examples of the stabilizer include sodium hydrogen sulfite, sodium pyrosulfite, potassium pyrosulfite, sodium pyrophosphate, sodium thiosulfate, sodium metasulfobenzoate, sodium formaldehyde sulfoxylate, ethylene diamine, edetate sodium, thioglycolic acid, sodium gluconate, potassium L-glutamate, L-lysine-L-glutamate, sodium chondroitin sulfate, albumin, L-aspartic acid, L-cysteine, and dibutylhydroxytoluene.

Examples of the surfactant include, sorbitan fatty acid ester, polyoxyethylene hydrogenated castor oil, polyoxyethylene sorbitan monolaurate, polyoxyethylene polyoxypropylene glycol, and polysorbate.

Examples of the soothing agent include lidocaine, procaine, meprylcaine, and benzyl alcohol.

Examples of the preservative include cresol, phenol, methyl paraoxybenzoate, ethyl paraoxybenzoate, benzalkonium chloride, and benzethonium chloride.

In an injectable preparation of the present invention, the dose of an active ingredient is appropriately determined in accordance with dosage form, age and gender of a patient, conditions of a disease, and other conditions; however, usually 0.1 to 100 mg/kg per adult per day may be administered.

In an injectable preparation of the present invention, the content of Compound A is 10 to 6000 mg, and preferably 100 to 2000 mg.

In an injectable preparation of the present invention, the content of the additives to be added for improving solubility is 0.1 to 100% (w/w), and preferably 3 to 50% (w/w) relative to the content of Compound A.

EXAMPLES

Hereinafter, the present invention will be described by showing Examples and Experimental Examples; however, the present invention is not limited to these examples.

The water content was measured by the Karl Fischer method.

Example 1

A suspension of Compound A (5.0 g) and sodium hydrogen carbonate (2.8 g) in water (35 mL) and 2-propanol (35 mL) was heated to 76° C. for dissolution. After 2-propanol (70 mL) was added dropwise at 40° C., the mixture was cooled to 5° C. and stirred at the same temperature for one hour. A solid substance was collected by filtration to obtain a yellow crystal of Salt A Hydrate 1 (5.3 g).

Water content: 5.5%

The obtained crystal (100.5 mg) was dissolved to distillated water (120 mL), and then potentiometric titration was conducted by using 0.1 mol/L hydrochloric acid. As a result, a crystal of monosodium salt was obtained.

Figure 1:
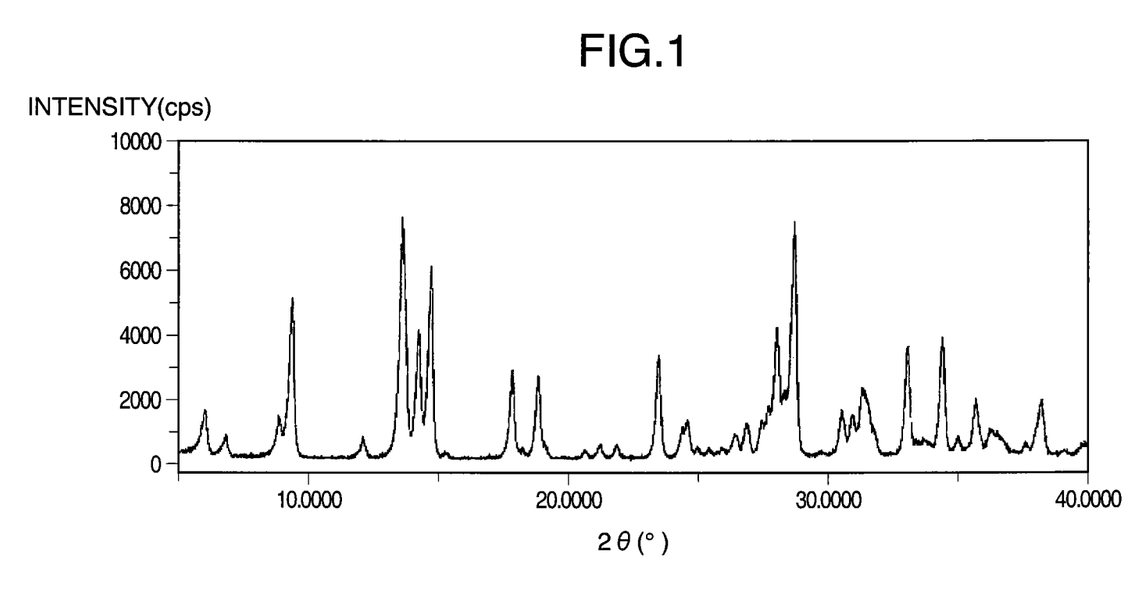
FIG. 1 is a powder X-ray diffraction pattern of a crystal of a sodium salt (Hydrate 1) of 6-fluoro-3-hydroxy-2-pyrazinecarboxamide.

The result of powder X-ray diffraction of the crystal is shown in FIG. 1 and Table 1.

Figure 4:
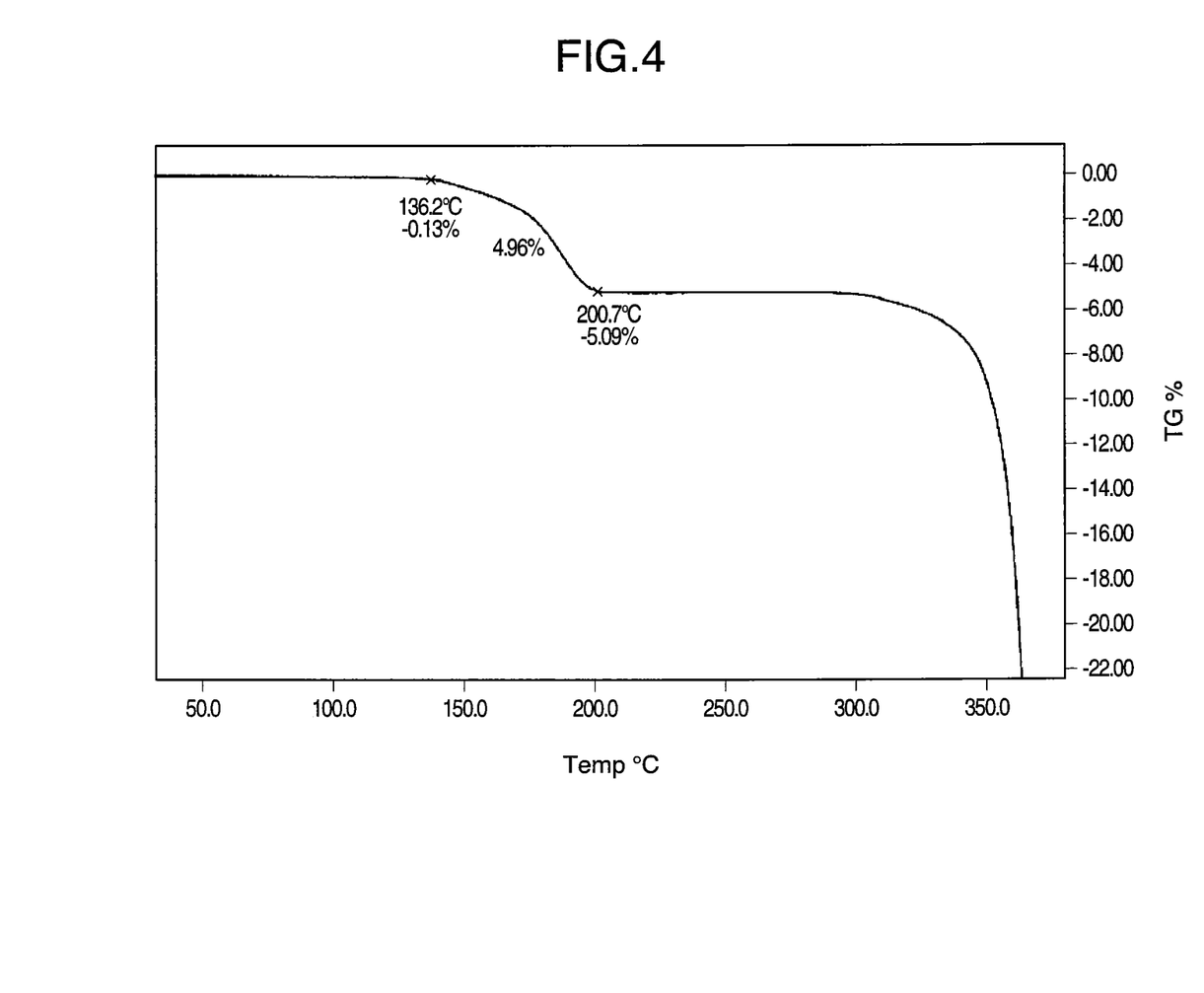
FIG. 4 is a thermogravimetric analysis pattern of a crystal of a sodium salt (Hydrate 1) of 6-fluoro-3-hydroxy-2-pyrazinecarboxamide.

The result of thermogravimetric analysis of the crystal is shown in FIG. 4. Weight of water (0.5 equivalent) was decreased at 136 to 201° C.

TABLE 1

| 2θ | d | Relative intensity |
|---|---|---|
| 9.4 | 9.45 | 66 |
| 13.6 | 6.51 | 97 |
| 14.2 | 6.23 | 49 |
| 14.7 | 6.03 | 78 |
| 17.8 | 4.98 | 38 |
| 18.8 | 4.71 | 36 |
| 23.4 | 3.79 | 46 |
| 28.0 | 3.19 | 49 |
| 28.6 | 3.12 | 100 |
| 33.0 | 2.71 | 51 |
| 34.3 | 2.61 | 53 |

Example 2

The crystal obtained in Example 1 was milled to obtain a powder. Each vial was filled with the powder (718 mg) to obtain an injectable preparation.

Example 3

To a suspension of Compound A (51.4 g) in Water for Injection was added 1 mol/L aqueous sodium hydroxide solution, and the mixture was stirred to dissolve Compound A. Thereafter, 1 mol/L aqueous sodium hydroxide solution was further added to adjust the pH to 8.5. To the solution was added Water for Injection to give a total volume of 600 mL. Thereafter, the mixture was filtered through a 0.22-μm membrane filter to obtain a liquid preparation (pH 8.5). The liquid preparation was cooled to 0° C. and stood still at the same temperature for four days. A solid substance was collected by filtration to obtain a yellow crystal of Salt A Hydrate 2.

Figure 2:
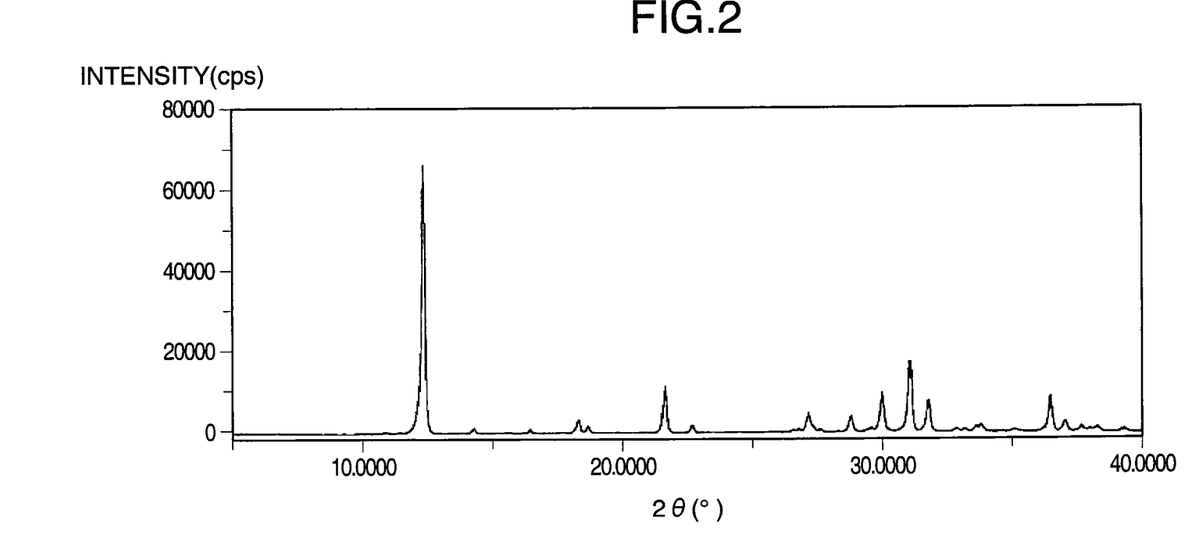
FIG. 2 is a powder X-ray diffraction pattern of a crystal of a sodium salt (Hydrate 2) of 6-fluoro-3-hydroxy-2-pyrazinecarboxamide.

The result of powder X-ray diffraction of the crystal is shown in FIG. 2 and Table 2.

Figure 5:
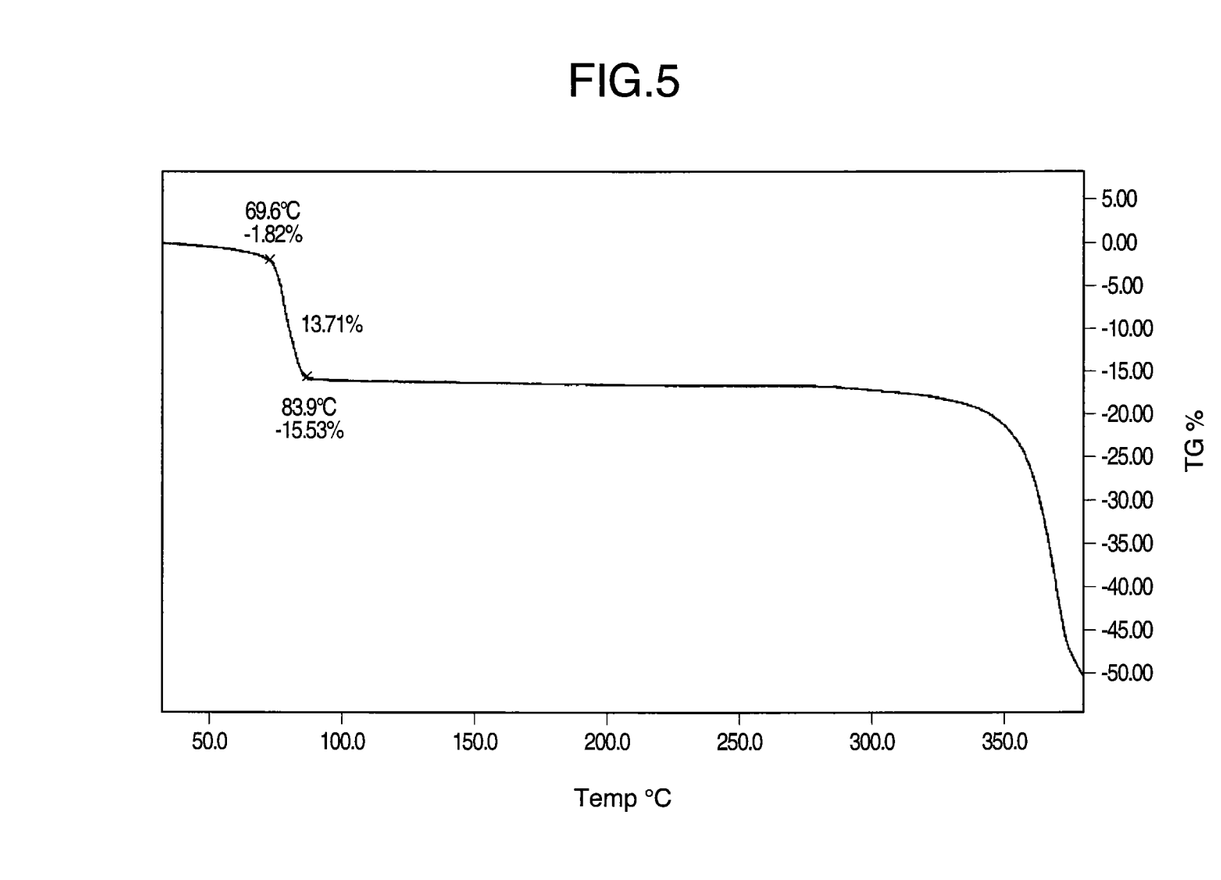
FIG. 5 is a thermogravimetric analysis pattern of a crystal of a sodium salt (Hydrate 2) of 6-fluoro-3-hydroxy-2-pyrazinecarboxamide (weight of water (1.5 equivalent) was decreased)
Figure 6:
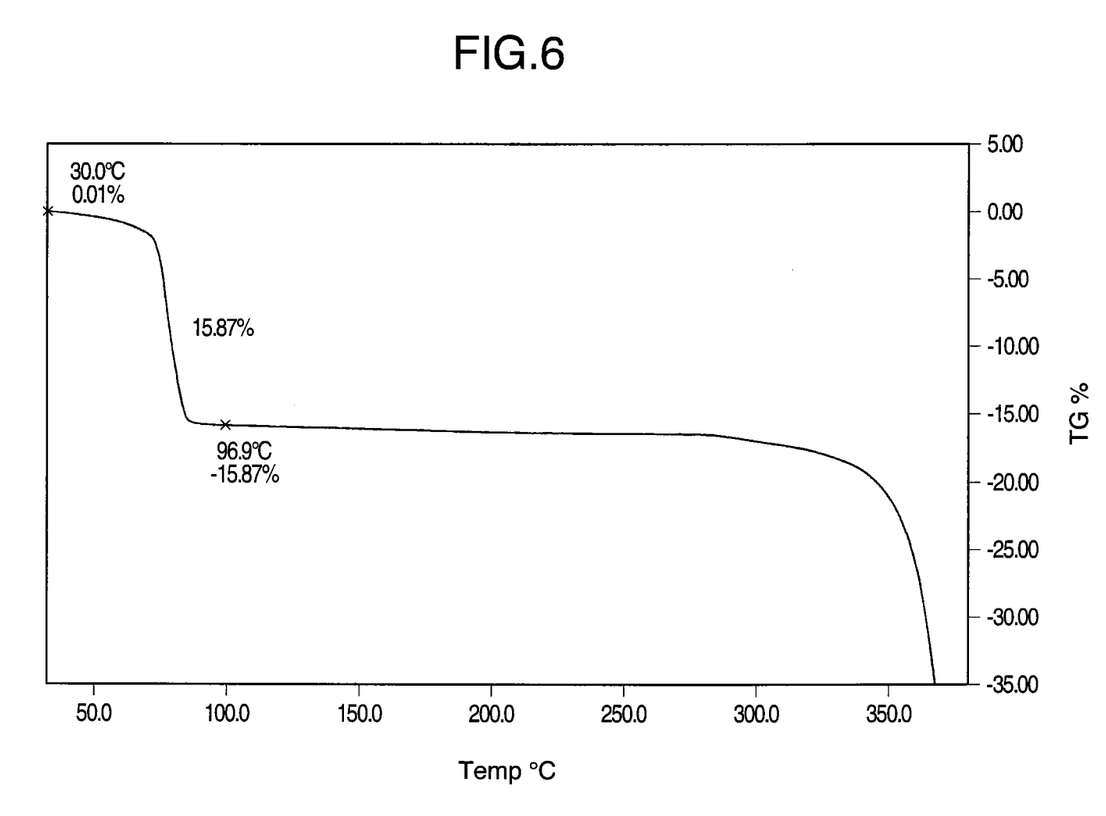
FIG. 6 is a thermogravimetric analysis pattern of a crystal of a sodium salt (Hydrate 2) of 6-fluoro-3-hydroxy-2-pyrazinecarboxamide (weight of water (2 equivalent) was decreased)

The result of thermogravimetric analysis of the crystal is shown in FIG. 5 and FIG. 6.

The thermogravimetric analysis was conducted at the temperature increase rate of 5° C./min.

Weight of water (1.5 equivalent) was decreased at 70 to 84° C. (FIG. 5). Weight of water (2.0 equivalent) was decreased at 30 to 97° C., (FIG. 6).

As a result of single crystal X-ray analysis, Salt A Hydrate 2 was found to be a dihydrate.

TABLE 2

| 2θ | d | Relative intensity |
|---|---|---|
| 10.0 | 8.85 | 100 |
| 20.1 | 4.42 | 19 |
| 29.2 | 3.06 | 16 |
| 30.3 | 2.95 | 34 |
| 31.1 | 2.87 | 14 |
| 36.2 | 2.48 | 16 |

Example 4

The crystal obtained in Example 3 was milled to obtain a powder. Each vial was filled with the powder (787 mg) to obtain an injectable preparation.

Example 5

Figure 3:
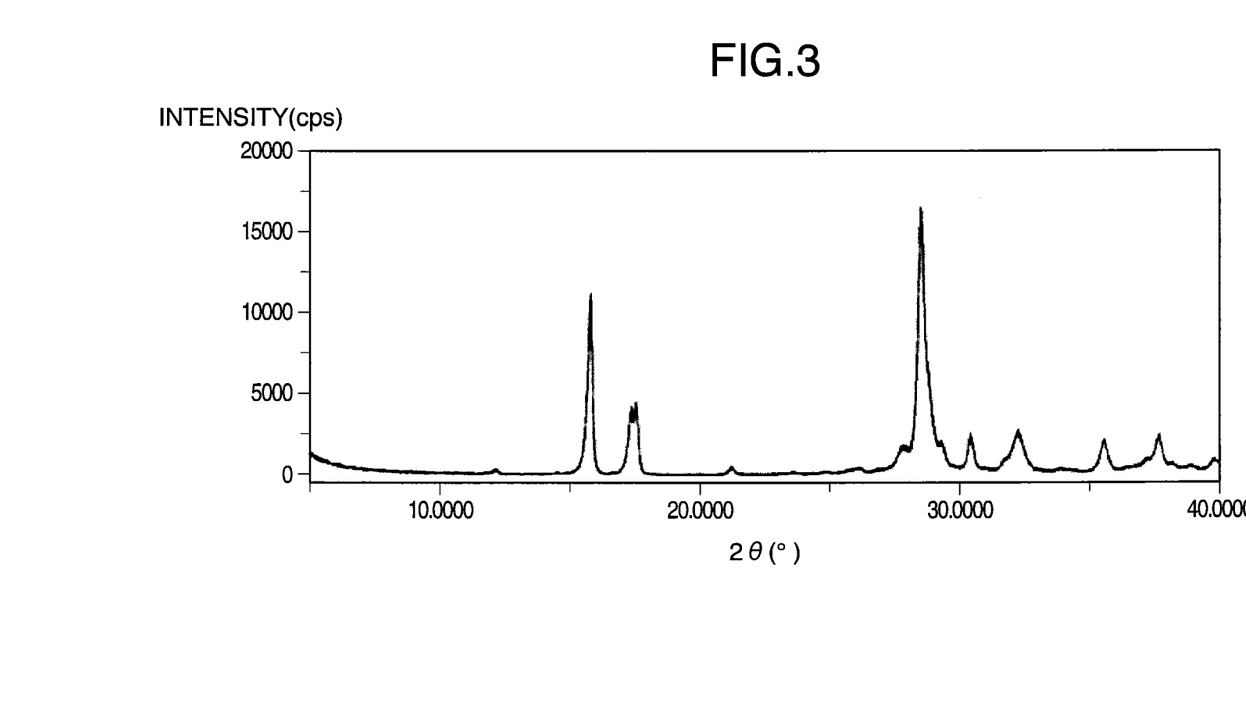
FIG. 3 is a powder X-ray diffraction pattern of a crystal of a sodium salt (anhydrate) of 6-fluoro-3-hydroxy-2-pyrazinecarboxamide.

The crystal (400 mg) obtained in Example 3 was allowed to stand still at 40° C. under vacuum (50 Pa or below) for 64 hours to obtain a crystal of an anhydrate.
Water content: 0.18%
The result of powder X-ray diffraction of the crystal is shown in FIG. 3 and Table 3.

TABLE 3

| 2θ | d | Relative intensity |
|---|---|---|
| 13.7 | 6.48 | 72 |
| 15.6 | 5.69 | 27 |
| 27.5 | 3.24 | 100 |
| 29.6 | 3.01 | 15 |
| 31.6 | 2.83 | 14 |
| 35.2 | 2.55 | 13 |

Example 6

To a suspension of Compound A (30.0 g) in Water for Injection was added 1 mol/L aqueous sodium hydroxide solution, and the mixture was stirred to dissolve Compound A. Thereafter, 1 mol/L aqueous sodium hydroxide solution was further added to adjust the pH to 8.5. To the solution was added Water for Injection to give a total volume of 400 mL. Thereafter, the mixture was filtered through a 0.22-μm membrane filter to obtain a liquid preparation (pH 8.4). Each vial was filled with the liquid preparation (8 mL), lyophilized, and then closed airtight to obtain a lyophilized preparation of a crystal.
Water content: 0.31%
The powder X-ray diffraction pattern of the lyophilized preparation was identical with that of example 5.
Lyophilization Method
1. Vials were cooled at a shelf temperature of −60° C. to freeze the content.
2. The temperature of the vials was increased to a shelf temperature of −5° C. and the vials were maintained at the same temperature for 24 hours.
3. The temperature of the vials was cooled to a shelf temperature of −55° C. or below and the vials were maintained at the same temperature for 2 hours.
4. The temperature of the vials was increased to a shelf temperature of 10° C. under vacuum (50 Pa or below) and the vials were maintained at the same pressure and temperature for 30 hours.
5. The temperature of the vials was increased to a shelf temperature of 20° C. and the vials were maintained at the same pressure and temperature for 2 hours.
6. The temperature of the vials was increased to a shelf temperature of 40° C. and the vials were maintained at the same pressure and temperature for 12 hours.

Example 7

To a suspension of Compound A (30.0 g) in Water for Injection (180 mL) was added 1 mol/L aqueous sodium hydroxide solution, and the mixture was stirred to dissolve Compound A. Thereafter, 1 mol/L aqueous sodium hydroxide solution was further added to adjust the pH to 8.5. To the solution was added Water for Injection to give a total volume of 400 mL. Thereafter, the mixture was filtered through a 0.22-μm membrane filter to obtain a liquid preparation (pH 8.4). Each vial was filled with the liquid preparation (8 mL), lyophilized, and then closed airtight to obtain a lyophilized preparation of a crystal.
Water content: 0.12%
The powder X-ray diffraction pattern of the lyophilized preparation was identical with that of example 5.
Lyophilization Method
1. Vials were cooled at a shelf temperature of −60° C. to freeze the content.
2. The temperature of the vials was increased to a shelf temperature of −10° C. and the vials were maintained at the same temperature for 24 hours.
3. The temperature of the vials was cooled to a shelf temperature of −55° C. or below and the vials were maintained at the same temperature for 2 hours.
4. The temperature of the vials was increased to a shelf temperature of 10° C. under vacuum (50 Pa or below) and the vials were maintained at the same pressure and temperature for 48 hours.
5. The temperature of the vials was increased to a shelf temperature of 20° C. and the vials were maintained at the same pressure and temperature for 2 hours.
6. The temperature of the vials was increased to a shelf temperature of 40° C. and the vials were maintained at the same pressure and temperature for 20 hours.

Example 8

To a suspension of Compound A (30.0 g) in Water for Injection was added 1 mol/L aqueous sodium hydroxide solution, and the mixture was stirred to dissolve Compound A. Thereafter, 1 mol/L aqueous sodium hydroxide solution was further added to adjust the pH to 8.5. To the solution was added Water for Injection to give a total volume of 400 mL and a solution (pH 8.5) was obtained. Thereafter, the mixture was filtered through a 0.22-μm membrane filter to obtain a liquid preparation. Each vial was filled with the liquid preparation (8 mL), lyophilized, and then closed airtight to obtain a lyophilized preparation of a crystal.
Water content: 0.37%
The powder X-ray diffraction pattern of the lyophilized preparation was identical with that of example 5.
Lyophilization Method
1. Vials were cooled at a shelf temperature of −60° C. to freeze the content.
2. The temperature of the vials was increased to a shelf temperature of −15° C. and the vials were maintained at the same temperature for 24 hours.

3. The temperature of the vials was cooled to a shelf temperature of −55° C. or below and the vials were maintained at the same temperature for 2 hours.
4. The temperature of the vials was increased to a shelf temperature of 10° C. under vacuum (50 Pa or below) and the vials were maintained at the same pressure and temperature for 24 hours.
5. The temperature of the vials was increased to a shelf temperature of 20° C. and the vials were maintained at the same pressure and temperature for 2 hours.
6. The temperature of the vials was increased to a shelf temperature of 40° C. and the vials were maintained at the same pressure and temperature for 12 hours.

Example 9

To a suspension of Compound A (75.0 g) in Water for Injection (420 mL) was added 1 mol/L aqueous sodium hydroxide solution, and the mixture was stirred to dissolve Compound A. Thereafter, 1 mol/L aqueous sodium hydroxide solution was further added to adjust the pH to 7.0. To the solution was added Water for Injection to give a total volume of 1000 mL. Thereafter, the mixture was filtered through a 0.22-μm membrane filter to obtain a liquid preparation (pH 7.0). Each vial was filled with the liquid preparation (8 mL), lyophilized, and then closed airtight to obtain a lyophilized preparation of a crystal.
  Water content: 0.08%
  The powder X-ray diffraction pattern of the lyophilized preparation was identical with that of example 5.
  Lyophilization Method
1. Vials were cooled at a shelf temperature of −60° C. to freeze the content.
2. The temperature of the vials was increased to a shelf temperature of −10° C. and the vials were maintained at the same temperature for 24 hours.
3. The temperature of the vials was cooled to a shelf temperature of −55° C. and the vials were maintained at the same temperature for 2 hours.
4. The temperature of the vials was increased to a shelf temperature of 40° C. under vacuum (50 Pa or below) and the vials were maintained at the same pressure and temperature for 70 hours.

Example 10

To a suspension of Compound A (46.2 g) in Water for Injection (1000 mL) was added 1 mol/L aqueous sodium hydroxide solution, and the mixture was stirred to dissolve Compound A. Thereafter, 1 mol/L aqueous sodium hydroxide solution was further added to adjust the pH to 8.5. To the solution was added Water for Injection to give a total volume of 1848 mL. Thereafter, the mixture was filtered through a 0.22-μm membrane filter to obtain a liquid preparation (pH 8.3). Each vial was filled with the liquid preparation (24 mL), lyophilized, and then closed airtight to obtain a lyophilized preparation of a crystal.
  Water content: 0.16%
  Lyophilization method: the same as in Example 9.

Example 11

To a suspension of Compound A (75.0 g) in Water for Injection (440 mL) was added 1 mol/L aqueous sodium hydroxide solution, and the mixture was stirred to dissolve Compound A. Thereafter, 1 mol/L aqueous sodium hydroxide solution was further added to adjust the pH to 7.0. To the solution was added Water for Injection to give a total volume of 1000 mL. To the solution (688 mL) was added Water for Injection (1376 mL). Thereafter, the mixture was filtered through a 0.22-μm membrane filter to obtain a liquid preparation (pH 7.0). Each vial was filled with the liquid preparation (24 mL), lyophilized, and then closed airtight to obtain a lyophilized preparation of a crystal.
  Water content: 0.17%
  Lyophilization method: the same as in Example 9.

Example 12

To a suspension of Compound A (24.0 g) in Water for Injection (140 mL) was added 1 mol/L aqueous sodium hydroxide solution, and the mixture was stirred to dissolve Compound A. Thereafter, 1 mol/L aqueous sodium hydroxide solution was further added to adjust the pH to 6.5. To the solution was added Water for Injection to give a total volume of 960 mL. Thereafter, the mixture was filtered through a 0.22-μm membrane filter to obtain a liquid preparation (pH 6.5). Each vial was filled with the liquid preparation (24 mL), lyophilized, and then closed airtight to obtain a lyophilized preparation of a crystal.
  Water content: 0.20%
  Lyophilization method: the same as in Example 9.

Example 13

To a suspension of Compound A (12.0 g) and L-leucine (2.00 g) in Water for Injection (380 mL) was added 1 mol/L aqueous sodium hydroxide solution, and the mixture was stirred to dissolve Compound A. Thereafter, 1 mol/L aqueous sodium hydroxide solution was further added to adjust the pH to 8.5. To the solution was added Water for Injection to give a total volume of 480 mL Thereafter, the mixture was filtered through a 0.22-μm membrane filter to obtain a liquid preparation (pH 8.4). Each vial was filled with the liquid preparation (24 mL), lyophilized, and then closed airtight to obtain a lyophilized preparation of a crystal.
  Water content: 0.27%
  Lyophilization method: the same as in Example 9.

Example 14

To a suspension of Compound A (12.0 g) and L-leucine (2.00 g) in Water for Injection (380 mL) was added 1 mol/L aqueous sodium hydroxide solution, and the mixture was stirred to dissolve Compound A. Thereafter, 1 mol/L aqueous sodium hydroxide solution was further added to adjust the pH to 8.0. To the solution was added Water for Injection to give a total volume of 480 mL. Thereafter, the mixture was filtered through a 0.22-μm membrane filter to obtain a liquid preparation (pH 7.9). Each vial was filled with the liquid preparation (24 mL), lyophilized, and then closed airtight to obtain a lyophilized preparation of a crystal.
  Water content: 0.27%
  Lyophilization method: the same as in Example 9.

Example 15

To a suspension of Compound A (12.0 g) and L-leucine (2.00 g) in Water for Injection (380 mL) was added 1 mol/L aqueous sodium hydroxide solution, and the mixture was stirred to dissolve Compound A. Thereafter, 1 mol/L aqueous sodium hydroxide solution was further added to adjust the pH to 7.5. To the solution was added Water for Injection to give a total volume of 480 mL. Thereafter, the mixture was filtered through a 0.22-μm membrane filter to obtain a liquid preparation (pH 7.4). Each vial was filled with the liquid preparation (24 mL), lyophilized, and then closed airtight to obtain a lyophilized preparation of a crystal.

Water content: 0.10%

Lyophilization method: the same as in Example 9.

Example 16

To a suspension of Compound A (12.0 g) and L-leucine (2.00 g) in Water for Injection (380 mL) was added 1 mol/L aqueous sodium hydroxide solution, and the mixture was stirred to dissolve Compound A. Thereafter, 1 mol/L aqueous sodium hydroxide solution was further added to adjust the pH to 7.0. To the solution was added Water for Injection to give a total volume of 480 mL. Thereafter, the mixture was filtered through a 0.22-μm membrane filter to obtain a liquid preparation (pH 7.0). Each vial was filled with the liquid preparation (24 mL), lyophilized, and then closed airtight to obtain a lyophilized preparation of a crystal.

Water content: 0.06%

In the powder X-ray diffraction pattern of the lyophilized preparation, the same peaks as those of the crystal of Salt A anhydrate observed in Example 5 were observed.

Lyophilization method: the same as in Example 9.

Example 17

To a suspension of Compound A (75.0 g) in Water for Injection (420 mL) was added 1 mol/L aqueous sodium hydroxide solution, and the mixture was stirred to dissolve Compound A. Thereafter, 1 mol/L aqueous sodium hydroxide solution was further added to adjust the pH to 7.0. To the solution was added Water for Injection to give a total volume of 1000 mL. To the solution (160 mL) was added taurine (2.00 g), and it was dissolved. Thereafter, the mixture was filtered through a 0.22-μm membrane filter to obtain a liquid preparation (pH 7.0). Each vial was filled with the liquid preparation (8 mL), lyophilized, and then closed airtight to obtain a lyophilized preparation of a crystal.

Water content: 0.22%

In the powder X-ray diffraction pattern of the lyophilized preparation, the same peaks as those of the crystal of Salt A anhydrate observed in Example 5 were observed.

Lyophilization method: the same as in Example 9.

Example 18

To a suspension of Compound A (75.0 g) in Water for Injection (420 mL) was added 1 mol/L aqueous sodium hydroxide solution, and the mixture was stirred to dissolve Compound A. Thereafter, 1 mol/L aqueous sodium hydroxide solution was further added to adjust the pH to 7.0. To the solution was added Water for Injection to give a total volume of 1000 mL. Thereafter, the mixture was filtered through a 0.22-μm membrane filter to obtain a liquid preparation (pH 7.0). Each vial was filled with the liquid preparation (8 mL) and L-histidine (0.10 g) was added to obtain a solution. Vials were lyophilized, and then closed airtight to obtain a lyophilized preparation of a crystal.

Lyophilization Method

1. Vials were cooled at a shelf temperature of −60° C. to freeze the content.
2. The temperature of the vials was increased to a shelf temperature of −10° C. and the vials were maintained at the same temperature for 24 hours.
3. The temperature of the vials was cooled to a shelf temperature of −55° C. or below and the vials were maintained at the same temperature for 2 hours.
4. The temperature of the vials was increased to a shelf temperature of 10° C. under vacuum (50 Pa or below) and the vials were maintained at the same pressure and temperature for 85 hours.
5. The temperature of the vials was increased to a shelf temperature of 20° C. and the vials were maintained at the same pressure and temperature for 2 hours.
6. The temperature of the vials was increased to a shelf temperature of 40° C. and the vials were maintained at the same pressure and temperature for 20 hours.

Example 19

To a suspension of Compound A (75.0 g) in Water for Injection (420 mL) was added 1 mol/L aqueous sodium hydroxide solution, and the mixture was stirred to dissolve Compound A. Thereafter, 1 mol/L aqueous sodium hydroxide solution was further added to adjust the pH to 7.0. To the solution was added Water for Injection to give a total volume of 1000 mL. Thereafter, the mixture was filtered through a 0.22-μm membrane filter to obtain a liquid preparation (pH 7.0). Each vial was filled with the liquid preparation (8 mL) and L-phenylalanine (0.10 g) was added to obtain a solution. Vials were lyophilized, and then closed airtight to obtain a lyophilized preparation of a crystal.

Lyophilization method: the same as in Example 9.

Example 20

To a suspension of Compound A (75.0 g) in Water for Injection (420 mL) was added 1 mol/L aqueous sodium hydroxide solution, and the mixture was stirred to dissolve Compound A. Thereafter, 1 mol/L aqueous sodium hydroxide solution was further added to adjust the pH to 7.0. To the solution was added Water for Injection to give a total volume of 1000 mL. Thereafter, the mixture was filtered through a 0.22-μm membrane filter to obtain a liquid preparation (pH 7.0). Each vial was filled with the liquid preparation (8 mL) and L-glutamine (0.30 g) was added to obtain a solution. Vials were lyophilized, and then closed airtight to obtain a lyophilized preparation of a crystal.

Lyophilization method: the same as in Example 9.

Example 21

To a suspension of Compound A (16.2 g) in Water for Injection was added 1 mol/L aqueous sodium hydroxide solution, and the mixture was stirred to dissolve Compound A. Thereafter, 1 mol/L aqueous sodium hydroxide solution was further added to adjust the pH to 7.0. To the solution was added Water for Injection to give a total volume of 216 mL. Thereafter, the mixture was filtered through a 0.22-μm membrane filter to obtain a liquid preparation. To the solution (40 mL) was added L-leucine (0.50 g) to obtain a solution (pH 7.0). Each vial was filled with the solution (8 mL), lyophilized, and then closed airtight to obtain a lyophilized preparation of a crystal.

Lyophilization method: the same as in Example 9.

Example 22

To a suspension of Compound A (24.0 g) and L-leucine (0.80 g) in Water for Injection (780 mL) was added 1 mol/L aqueous sodium hydroxide solution, and the mixture was stirred to dissolve Compound A. Thereafter, 1 mol/L aqueous sodium hydroxide solution was further added to adjust the pH to 7.0. To the solution was added Water for Injection to give a total volume of 960 mL. Thereafter, the mixture was filtered through a 0.22-μm membrane filter to obtain a liquid preparation (pH 7.0). Each vial was filled with the liquid preparation (24 mL), lyophilized, and then closed airtight to obtain a lyophilized preparation of a crystal.

Water content: 0.10%

Lyophilization method: the same as in Example 9.

Example 23

To a suspension of Compound A (24.0 g) in Water for Injection (780 mL) was added 1 mol/L aqueous sodium hydroxide solution, and the mixture was stirred to dissolve Compound A. Thereafter, 1 mol/L aqueous sodium hydroxide solution was further added to adjust the pH to 7.0. To the solution was added Water for Injection to give a total volume of 960 mL. Thereafter, the mixture was filtered through a 0.22-μm membrane filter to obtain a liquid preparation (pH 7.0). To the solution (72 mL) was added L-alanine (0.30 g) to obtain a solution. Each vial was filled with the solution (24 mL), lyophilized, and then closed airtight to obtain a lyophilized preparation of a crystal.

Lyophilization method: the same as in Example 9.

Example 24

To a suspension of Compound A (67.5 g) in Water for Injection (400 mL) was added 1 mol/L aqueous sodium hydroxide solution, and the mixture was stirred to dissolve Compound A. Thereafter, 1 mol/L aqueous sodium hydroxide solution was further added to adjust the pH to 7.0. To the solution was added Water for Injection to give a total volume of 900 mL. To the solution (800 mL) was added the Water for Injection (1600 mL), and the mixture was filtered through a 0.22-μm membrane filter to obtain a liquid preparation. To the solution (240 mL) was added L-isoleucine (0.20 g) to obtain a solution (pH 6.9). Each vial was filled with the solution (24 mL), lyophilized, and then closed airtight to obtain a lyophilized preparation of a crystal.

Lyophilization method: the same as in Example 9.

Example 25

To a suspension of Compound A (67.5 g) in Water for Injection (400 mL) was added 1 mol/L aqueous sodium hydroxide solution, and the mixture was stirred to dissolve Compound A. Thereafter, 1 mol/L aqueous sodium hydroxide solution was further added to adjust the pH to 7.0. To the solution was added Water for Injection to give a total volume of 900 mL. To the solution (800 mL) was added the Water for Injection (1600 mL) to obtain a liquid preparation. To the solution (600 mL) was added L-isoleucine (2.50 g), and it was dissolved. Thereafter, the mixture was filtered through a 0.22-μm membrane filter to obtain a liquid preparation (pH 6.9). Each vial was filled with the liquid preparation (24 mL), lyophilized, and then closed airtight to obtain a lyophilized preparation of a crystal.

Water content: 0.12%

Lyophilization method: the same as in Example 9.

Example 26

To a suspension of Compound A (67.5 g) in Water for Injection (400 mL) was added 1 mol/L aqueous sodium hydroxide solution, and the mixture was stirred to dissolve Compound A. Thereafter, 1 mol/L aqueous sodium hydroxide solution was further added to adjust the pH to 7.0. To the solution was added Water for Injection to give a total volume of 900 mL. To the solution (800 mL) was added the Water for Injection (1600 mL). Thereafter, the mixture was filtered through a 0.22-μm membrane filter to obtain a liquid preparation. To the liquid preparation (96 mL) was added L-valine (0.41 g), and a solution (pH 6.9) was obtained. Each vial was filled with the solution (24 mL), lyophilized, and then closed airtight to obtain a lyophilized preparation of a crystal.

Lyophilization method: the same as in Example 9.

Example 27

To a suspension of Compound A (24.0 g) in Water for Injection (780 mL) was added 1 mol/L aqueous sodium hydroxide solution, and the mixture was stirred to dissolve Compound A. Thereafter, 1 mol/L aqueous sodium hydroxide solution was further added to adjust the pH to 7.0. To the solution was added Water for Injection to give a total volume of 960 mL. Thereafter, the mixture was filtered through a 0.22-μm membrane filter to obtain a liquid preparation (pH 7.0). To the liquid preparation (72 mL) was added DL-methionine (0.30 g), and a solution was obtained. Each vial was filled with the solution (24 mL), lyophilized, and then closed airtight to obtain a lyophilized preparation of a crystal.

Lyophilization method: the same as in Example 9.

Example 28

To a suspension of Compound A (30.0 g) and urea (5.00 g) in Water for Injection (150 mL) was added 1 mol/L aqueous sodium hydroxide solution, and the mixture was stirred to dissolve Compound A. Thereafter, 1 mol/L aqueous sodium hydroxide solution was further added to adjust the pH to 8.5. To the solution was added Water for Injection to give a total volume of 400 mL. Thereafter, the mixture was filtered through a 0.22-μm membrane filter to obtain a liquid preparation (pH 8.5). Each vial was filled with the liquid preparation (8 mL), lyophilized, and then closed airtight to obtain a lyophilized preparation of a crystal.

Water content: 0.89%

Lyophilization method: the same as in Example 7.

Example 29

To a suspension of Compound A (75.0 g) in Water for Injection (440 mL) was added 1 mol/L aqueous sodium hydroxide solution, and the mixture was stirred to dissolve Compound A. Thereafter, 1 mol/L aqueous sodium hydroxide solution was further added to adjust the pH to 7.0. To the solution was added Water for Injection to give a total volume of 1000 mL. To the solution (688 mL) was added the Water for Injection (1376 mL). Thereafter, the mixture was filtered through a 0.22-μm membrane filter to obtain a liquid preparation (pH 7.0). To the liquid preparation (106 mL) was added polysorbate 80 (35.0 mg), and a solution was obtained. Each vial was filled with the solution (24 mL), lyophilized, and then closed airtight to obtain a lyophilized preparation of a crystal.

Lyophilization method: the same as in Example 9.

Example 30

To a suspension of Compound A (25.0 g) in Water for Injection (800 mL) was added 1 mol/L aqueous sodium hydroxide solution, and the mixture was stirred to dissolve Compound A. Thereafter, 1 mol/L aqueous sodium hydroxide solution was further added to adjust the pH to 7.0. To the solution was added Water for Injection to give a total volume of 1000 mL. To the solution (600 mL) was added polyethylene glycol 400 (2.60 g), and it was dissolved. Thereafter, the mixture was filtered through a 0.22-μm membrane filter to obtain a liquid preparation (pH 7.0). Each vial was filled with the liquid preparation (24 mL), lyophilized, and then closed airtight to obtain a lyophilized preparation of a crystal.
Water content: 0.02%
Lyophilization method: the same as in Example 9.

Example 31

To a suspension of Compound A (75.0 g) in Water for Injection (420 mL) was added 1 mol/L aqueous sodium hydroxide solution, and the mixture was stirred to dissolve Compound A. Thereafter, 1 mol/L aqueous sodium hydroxide solution was further added to adjust the pH to 7.0. To the solution was added Water for Injection to give a total volume of 1000 mL. To the solution (264 mL) was added the Water for Injection (726 mL). Thereafter, the mixture was filtered through a 0.22-μm membrane filter to obtain a liquid preparation (pH 6.9). Each vial was filled with the liquid preparation (30 mL) and dextran 40 (0.30 g) was added to obtain a solution. Vials were lyophilized, and then closed airtight to obtain a lyophilized preparation of a crystal.
Lyophilization method: the same as in Example 9.

Comparative Example 1

To a suspension of Compound A (13.8 g) in Water for Injection (50 mL) was added 1 mol/L aqueous sodium hydroxide solution, and the mixture was stirred to dissolve Compound A. Thereafter, 1 mol/L aqueous sodium hydroxide solution was further added to adjust the pH to 8.5. To the solution was added Water for Injection to give a total volume of 161 mL. Thereafter, the mixture was filtered through a 0.22-μm membrane filter to obtain a liquid preparation (pH 8.4). Each vial was filled with the liquid preparation (7 mL), lyophilized, and then closed airtight to obtain a lyophilized preparation of an amorphous product.
Water content: 2.2%
Lyophilization Method
1. Vials were cooled at a shelf temperature of −60° C. to freeze the content.
2. The temperature of the vials was increased to a shelf temperature of −10° C. under vacuum (50 Pa or below) and the vials were maintained at the same pressure and temperature for 37 hours.
3. The temperature of the vials was increased to a shelf temperature of 0° C. and the vials were maintained at the same pressure and temperature for 9 hours.
4. The temperature of the vials was increased to a shelf temperature of 10° C. and the vials were maintained at the same pressure and temperature for 4 hours.
5. The temperature of the vials was increased to a shelf temperature of 20° C. and the vials were maintained at the same pressure and temperature for 4 hours.
6. The temperature of the vials was increased to a shelf temperature of 40° C. and the vials were maintained at the same pressure and temperature for 15 hours.

Comparative Example 2

To a suspension of Compound A (12.0 g) in Water for Injection (70 mL) was added 1 mol/L aqueous sodium hydroxide solution, and the mixture was stirred to dissolve Compound A. Thereafter, 1 mol/L aqueous sodium hydroxide solution was further added to adjust the pH to 8.5. To the solution was added Water for Injection to give a total volume of 160 mL. Thereafter, the mixture was filtered through a 0.22-μm membrane filter to obtain a liquid preparation (pH 8.5). Each vial was filled with the liquid preparation (8 mL), lyophilized, and then closed airtight to obtain a lyophilized preparation of an amorphous product.
Lyophilization Method
1. Vials were cooled at a shelf temperature of −60° C. to freeze the content.
2. The temperature of the vials was increased to a shelf temperature of 50° C. under vacuum (50 Pa or below) and the vials were maintained at the same pressure and temperature for 39 hours.

Test Example 1

Solubility

To the each vial obtained in Examples and Comparative Examples was added Water for Injection (10 mL) and the vials were shaken by hand. Thus, the dissolution time of the solid substance was measured. The results are shown in Table 4.

TABLE 4

| Example No. | Dissolution time (seconds) |
| --- | --- |
| 2 | 15 |
| 4 | 20 |
| 7 | 25 |
| 9 | 22 |
| 10 | 26 |
| 11 | 14 |
| 12 | 13 |
| 13 | 19 |
| 14 | 13 |
| 15 | 7 |
| 16 | 6 |
| 17 | 18 |
| 18 | 17 |
| 19 | 15 |
| 20 | 9 |
| 21 | 13 |
| 22 | 16 |
| 23 | 16 |
| 24 | 15 |
| 25 | 9 |
| 26 | 9 |
| 27 | 11 |
| 28 | 10 |
| 29 | 14 |
| 30 | 6 |
| 31 | 13 |
| Comparative Example 1 | 60 |
| Comparative Example 2 | 65 |

The dissolution time of an amorphous product (Comparative Example 1) was 60 seconds. The dissolution time of an amorphous product (Comparative Example 2) was 65 seconds.
On the other hand, the dissolution time of milled Hydrate 1 (Example 2) and milled Hydrate 2 (Example 4) was 15 seconds and 20 seconds, respectively. The milled crystals exhibited more superior solubility than the amorphous product.
The dissolution time of preparation (Example 7) produced by lyophilization including an annealing step was 25 seconds.

The preparation produced by this process exhibited more superior solubility than the amorphous product even though it is not milled.

The dissolution time of preparation (Example 9) produced by lyophilizing a solution adjusted to pH 7.0 in the same manner as in Example 7 was 22 seconds. The preparation in Example 9 exhibited much more superior solubility than the preparation in Example 7.

The dissolution time of preparation (Example 10) produced by lyophilizing a solution (24 mL) adjusted to pH 8.5 according to the process of Example 7 was 26 seconds. On the other hand, the dissolution time of preparation (Example 11) produced by lyophilizing a solution (24 mL) adjusted to pH 7.0 was 14 seconds. The dissolution time of preparation (Example 12) produced by lyophilizing a solution (24 mL) adjusted to pH 6.5 was 13 seconds. The dissolution time was shortened by reducing pH value.

The dissolution time of preparation (Example 13) containing L-leucine as additives and produced by lyophilizing a solution (24 mL) adjusted to pH 8.5 was 19 seconds. The dissolution time of preparation (Example 13) was shorter than that of preparation (Example 10) not containing L-leucine.

Moreover, the dissolution time of preparations (Examples 14 to 16) produced by reducing pH value was 6 to 13 seconds. The dissolution time was shortened by reducing pH value.

The dissolution time of preparations containing amino acids as additives (Examples 17 to 27), preparation containing urea as additives (Example 28), preparation containing polysorbate 80 as additives (Example 29), preparation containing polyethylene glycol 400 as additives (Example 30), and preparation containing dextran 40 as additives (Example 31) all fall within the range of 20 seconds, and these preparations exhibit much more superior solubility than an amorphous product.

Test Example 2

Stability (1)

The preparations of Examples 1, 7, 9, 10, 11, 12, 25, 28 and 29 were allowed to stand still at 60° C. for 1 month and then their appearance was observed. As a result, appearance change was not observed.

Test Example 4

Stability (2)

The preparations of Examples 1, 10, 15, 16, 22 and Comparative Example 1 were irradiated (1,200,000 lx·hr) by a D65 lamp (FLR20S-D-EDL-D65/M) and then their appearance was observed. As a result, appearance change was not observed in the preparations of Examples 1, 10, 15, 16 and 22; whereas the preparation of Comparative Example 1 turned into orange-yellow.

INDUSTRIAL APPLICABILITY

A preparation filled with a crystal of a sodium salt of 6-fluoro-3-hydroxy-2-pyrazinecarboxamide of the present invention is superior in solubility and useful as an injectable preparation.

The invention claimed is:
1. A process for producing a lyophilized preparation containing a crystal of a sodium salt of 6-fluoro-3-hydroxy-2-pyrazinecarboxamide, comprising the steps:
   (1) cooling an aqueous solution containing a sodium salt of 6-fluoro-3-hydroxy-2-pyrazinecarboxamide to produce a frozen product;
   (2) increasing the temperature of the frozen product within the range of −15° C. to −5° C.;
   (3) cooling the frozen product again; and
   (4) carrying out lyophilization.

* * * * *